(12) United States Patent
Bailey et al.

(10) Patent No.: US 9,149,287 B2
(45) Date of Patent: *Oct. 6, 2015

(54) FEMORAL CUT GUIDE

(71) Applicant: Zimmer, Inc., Warsaw, IN (US)

(72) Inventors: Aaron M Bailey, Round Rock, TX (US); Kevin S. Cook, Warsaw, IN (US); Christopher M. Byrd, Elkhart, IN (US); Prashanth Hegde, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/624,252

(22) Filed: Feb. 17, 2015

(65) Prior Publication Data

US 2015/0157342 A1 Jun. 11, 2015

Related U.S. Application Data

(60) Continuation of application No. 14/299,643, filed on Jun. 9, 2014, now Pat. No. 8,986,310, which is a division of application No. 12/844,495, filed on Jul. 27, 2010, now Pat. No. 8,771,280.

(60) Provisional application No. 61/311,443, filed on Mar. 8, 2010.

(51) Int. Cl.
*A61B 17/17* (2006.01)
*A61B 17/56* (2006.01)
(Continued)

(52) U.S. Cl.
CPC ............. *A61B 17/1764* (2013.01); *A61B 17/56* (2013.01); *A61F 2/389* (2013.01); *A61F 2/3859* (2013.01)

(58) Field of Classification Search
CPC ..... A61B 17/15; A61B 17/154; A61B 17/155
USPC .............................. 606/79, 82, 86 R, 88, 89; 623/20.14–20.35
See application file for complete search history.

(56) References Cited

U.S. PATENT DOCUMENTS

| 5,100,409 A | 3/1992 | Coates et al. |
| 5,176,684 A | 1/1993 | Ferrante et al. |

(Continued)

FOREIGN PATENT DOCUMENTS

WO WO-2008054389 A1 5/2008

OTHER PUBLICATIONS

"U.S. Appl. No. 12/844,495, Non Final Office Action mailed Jan. 4, 2013", 16 pgs.

(Continued)

*Primary Examiner* — Christian Sevilla
*Assistant Examiner* — Eric S. Gibson
(74) *Attorney, Agent, or Firm* — Schwegman Lundberg & Woessner, P.A.

(57) ABSTRACT

The present disclosure provides a femoral cut guide for preparing a distal femur to receive a prosthetic femoral component of a knee implant. The prosthetic femoral component includes a central box. The femoral cut guide replicates the size and shape of the prosthetic femoral component, such that the femoral cut guide may serve as a trial or provisional component used to reduce and test the prepared knee joint before implanting the final prosthetic femoral component. The femoral cut guide includes a detachable box cut guide for preparing the distal femur to receive the central box of the prosthetic femoral component.

20 Claims, 10 Drawing Sheets

(51) Int. Cl.
*A61B 17/58* (2006.01)
*A61F 2/38* (2006.01)

(56) References Cited

U.S. PATENT DOCUMENTS

| | | | |
|---|---|---|---|
| 5,415,662 | A | 5/1995 | Ferrante et al. |
| 5,569,259 | A * | 10/1996 | Ferrante et al. ................ 606/87 |
| 5,601,563 | A * | 2/1997 | Burke et al. ................ 606/86 R |
| 5,769,854 | A | 6/1998 | Bastian et al. |
| 7,744,600 | B2 * | 6/2010 | Rangaiah et al. ............... 606/88 |
| 7,963,968 | B2 | 6/2011 | Dees, Jr. |
| 8,002,777 | B2 * | 8/2011 | Fox et al. ........................ 606/88 |
| 8,038,681 | B2 | 10/2011 | Koenemann |
| 8,187,280 | B2 * | 5/2012 | May et al. ........................ 606/88 |
| 8,377,141 | B2 * | 2/2013 | McMinn ................... 623/20.35 |
| 8,425,524 | B2 | 4/2013 | Aker et al. |
| 8,771,280 | B2 | 7/2014 | Bailey et al. |
| 8,986,310 | B2 | 3/2015 | Bailey et al. |
| 2004/0039450 | A1 * | 2/2004 | Griner et al. ............... 623/20.31 |
| 2004/0078043 | A1 * | 4/2004 | Masini ............................ 606/88 |
| 2004/0153087 | A1 * | 8/2004 | Sanford et al. ................. 606/88 |
| 2005/0192588 | A1 * | 9/2005 | Garcia ............................ 606/88 |
| 2006/0173463 | A1 * | 8/2006 | Dees ............................... 606/88 |
| 2006/0195113 | A1 | 8/2006 | Masini |
| 2006/0241634 | A1 * | 10/2006 | Tuttle et al. .................... 606/86 |
| 2007/0073305 | A1 | 3/2007 | Lionberger et al. |
| 2007/0173850 | A1 | 7/2007 | Rangaiah et al. |
| 2008/0312659 | A1 | 12/2008 | Metzger et al. |
| 2009/0088762 | A1 * | 4/2009 | Koenemann ................... 606/88 |
| 2009/0088763 | A1 * | 4/2009 | Aram et al. .................... 606/88 |
| 2010/0076441 | A1 * | 3/2010 | May et al. ....................... 606/79 |
| 2011/0218541 | A1 * | 9/2011 | Bailey et al. ................... 606/88 |
| 2011/0307067 | A1 * | 12/2011 | Dees .......................... 623/20.35 |
| 2013/0165936 | A1 * | 6/2013 | Myers ............................. 606/80 |
| 2014/0288564 | A1 | 9/2014 | Bailey et al. |

OTHER PUBLICATIONS

"U.S. Appl. No. 12/844,495, Non Final Office Action mailed Aug. 22, 2014", 14 pgs.

"U.S. Appl. No. 12/844,495, Notice of Allowance mailed Feb. 24, 2014", 10 pgs.

"U.S. Appl. No. 12/844,495, Response filed Apr. 30, 2013 to Non Final Office Action mailed Jan. 4, 2013", 13 pgs.

"U.S. Appl. No. 12/844,495, Response filed Nov. 21, 2013 to Non-Final Office Action mailed Aug. 22, 2013", 15 pgs.

"U.S. Appl. No. 12/844,495, Restriction Requirement mailed Sep. 26, 2012", 6 pgs.

"U.S. Appl. No. 14/299,643, Corrected Notice of Allowance mailed Nov. 21, 2014", 2 pgs.

"U.S. Appl. No. 14/299,643, Non Final Office Action mailed Jul. 31, 2014", 11 pgs.

"U.S. Appl. No. 14/299,643, Notice of Allowance mailed Nov. 12, 2014", 8 pgs.

"U.S. Appl. No. 14/299,643, Response filed Oct. 31, 2014 to Non-Final Office Action mailed Jul. 31, 2014", 10 pgs.

"NexGen LPS-Flex Mobile and LPS-Mobile Bearing Knees", Zimmer, Inc., (2007, 2008), 4 pgs.

"Surgical Technique, Zimmer Revision LCCK Instrumentation Surgical Technique for Legacy Constrained Condylar", Zimmer 2001, 2007, 2008 97-5994-302-00 Rev.3, (2001), 108 pgs.

* cited by examiner

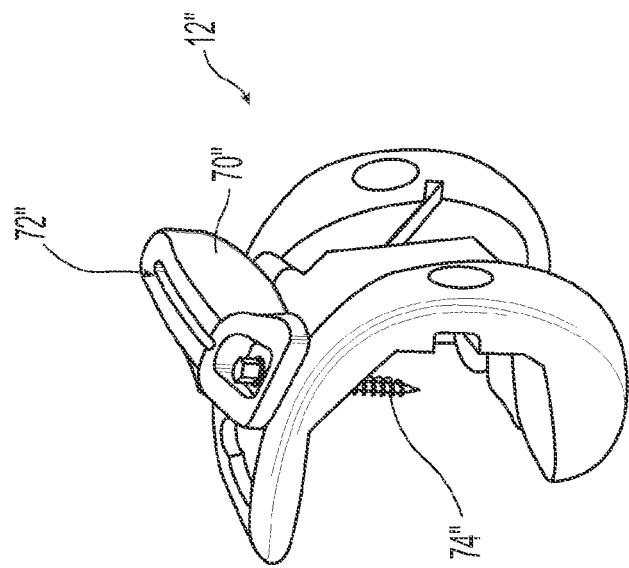
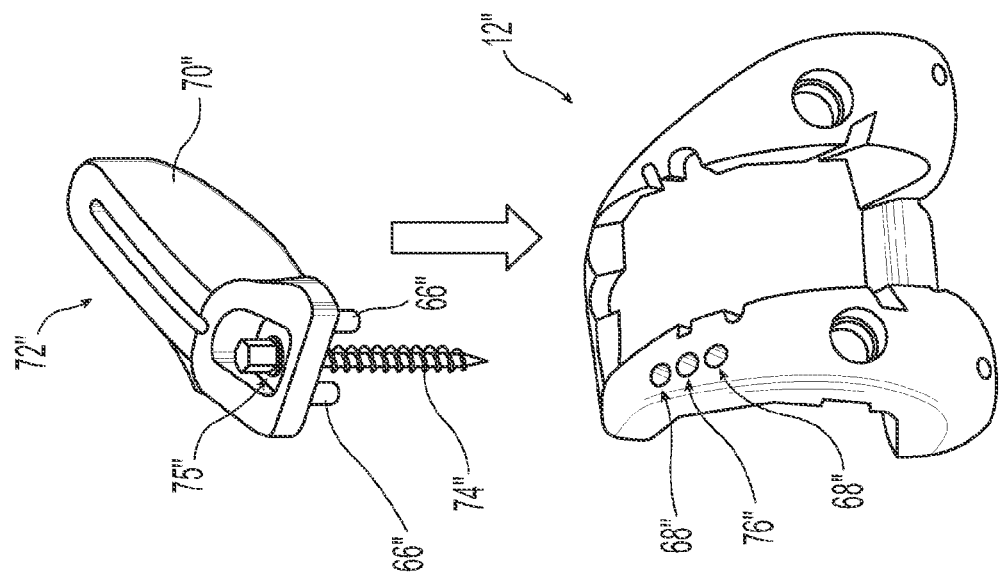

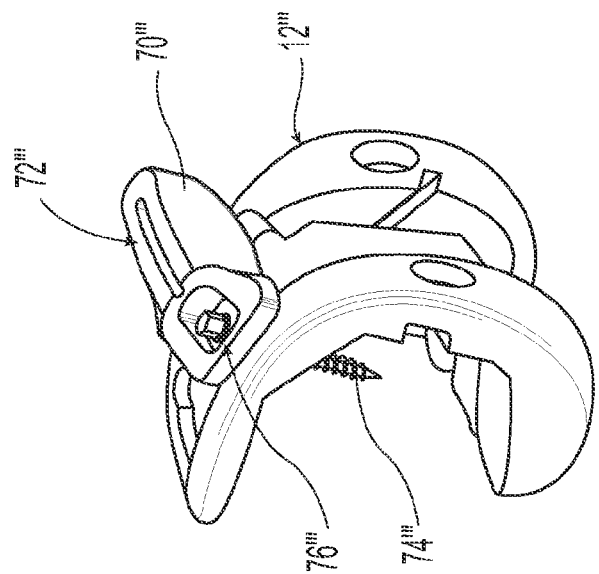
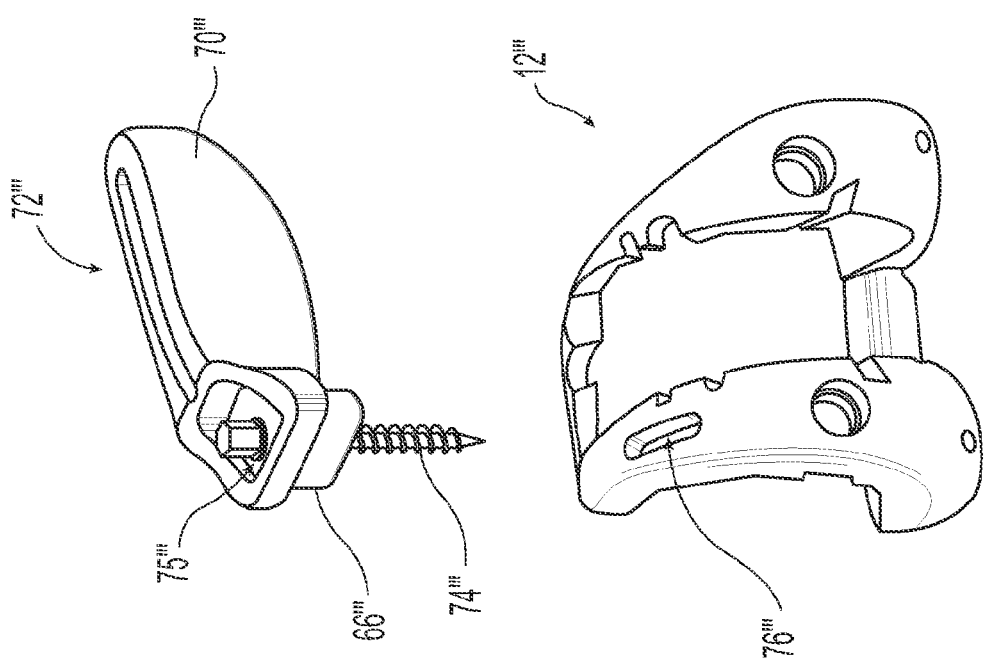

FEMORAL CUT GUIDE

CROSS-REFERENCE TO RELATED APPLICATIONS

This application is a continuation of U.S. patent application Ser. No. 14/299,643, filed Jun. 9, 2014, which is a divisional of U.S. patent application Ser. No. 12/844,495, filed Jul. 27, 2010, now issued as U.S. Pat. No. 8,771,280, which claims priority from U.S. Provisional Patent Application Ser. No. 61/311,443, entitled "FEMORAL CUT GUIDE," filed Mar. 8, 2010, the disclosures of which are hereby expressly incorporated by reference herein in their entirety.

BACKGROUND

1. Field of the Invention

The present invention relates to orthopedic cut guides. More particularly, the present invention relates to femoral cut guides and methods for using the same.

2. Description of the Related Art

In a natural knee joint, the distal end of the femur articulates against the proximal end of the tibia. The knee joint is supported by various ligaments, including the posterior cruciate ligament (PCL) and the anterior cruciate ligament (ACL). These ligaments stabilize the knee joint and cooperate to control the complex movements of the knee joint during flexion and extension. The PCL, in particular, originates at the distal femur and attaches to the posterior side of the proximal tibia to resist posterior translation of the tibia relative to the femur.

When the natural knee joint becomes damaged, a knee arthroplasty procedure may be performed to resect the distal femur and/or the proximal tibia and to replace with resected bones with prosthetic components that are designed to simulate articulation of the natural knee joint. It may also be necessary during the knee arthroplasty procedure to sacrifice certain ligaments of the knee joint, such as the PCL. In those cases, the prosthetic knee components may also be designed to simulate the behavior of the sacrificed ligament. For example, if the PCL is sacrificed, the prosthetic femoral component and the prosthetic tibial component may be stabilized posteriorly to resist posterior translation of the prosthetic tibial component relative to the prosthetic femoral component.

SUMMARY

The present disclosure provides a femoral cut guide for preparing a distal femur to receive a prosthetic femoral component of a knee implant. The prosthetic femoral component includes a central box. The femoral cut guide replicates the size and shape of the prosthetic femoral component, such that the femoral cut guide may serve as a trial or provisional component used to reduce and test the prepared knee joint before implanting the final prosthetic femoral component. The femoral cut guide includes a detachable box cut guide for preparing the distal femur to receive the central box of the prosthetic femoral component.

According to an embodiment of the present invention, a femoral cut guide is provided for preparing a distal femur to receive a prosthetic femoral component. The prosthetic femoral component includes a first articulating surface and an opposing first bone-contacting surface that rests against the distal femur, the first bone-contacting surface including a first anterior portion, a first distal portion, and a first posterior portion. The prosthetic femoral component further includes a box that projects proximally from the first distal portion of the first bone-contacting surface. The femoral cut guide includes a body having a second articulating surface that is shaped to replicate the first articulating surface and a second bone-contacting surface that is shaped to replicate the first bone-contacting surface, the second bone-contacting surface including a second anterior portion, a second distal portion, and a second posterior portion. The femoral cut guide also includes a box cut guide removably coupled to the body, the box cut guide including a reference surface located in a cut plane, the reference surface located proximally of the second distal portion of the second bone-contacting surface when the box cut guide is coupled to the body, whereby the reference surface of the box cut guide guides a cutting tool in the cut plane to remove bone from the distal femur so as to accommodate the box when the prosthetic femoral component is secured to the distal femur.

According to another embodiment of the present invention, a femoral cut guide is provided for preparing a distal femur to receive a prosthetic femoral component. The prosthetic femoral component includes a first articulating surface and an opposing first bone-contacting surface that rests against the distal femur, the prosthetic femoral component further including a central box that projects proximally from the first bone-contacting surface. The femoral cut guide includes a body having a second articulating surface that is shaped to replicate the first articulating surface and a second bone-contacting surface that is shaped to replicate the first bone-contacting surface, the body including a medial side and a lateral side that define a central opening therebetween. The femoral cut guide also includes a box cut guide removably coupled to the body, the box cut guide including at least one elongate guide slot that is sized to receive a cutting tool therein, the elongate guide slot extending from the medial side to the lateral side of the body across the central opening in the body when the box cut guide is coupled to the body, whereby the box cut guide guides the cutting tool through the elongate guide slot and across the central opening in the body to remove bone from the distal femur so as to accommodate the central box when the prosthetic femoral component is secured to the distal femur.

According to yet another embodiment of the present invention, a method is provided for preparing a distal femur to receive a prosthetic femoral component, the prosthetic femoral component including a first articulating surface, an opposing first bone-contacting surface, and a box that projects proximally from the first bone-contacting surface to a top surface. The method includes the steps of: providing a body having a second articulating surface that is shaped to replicate the first articulating surface and a second bone-contacting surface that is shaped to replicate the first bone-contacting surface; positioning the second bone-contacting surface of the body against the distal femur; attaching a box cut guide to the body, the box cut guide including a reference surface located in a cut plane; guiding a cutting tool across the reference surface of the box cut guide to prepare a resected surface of the distal femur, the resected surface of the distal femur located in the cut plane; removing the body from the distal femur; and positioning the first bone-contacting surface of the prosthetic femoral component against the distal femur with the top surface of the box bordering the resected surface of the distal femur.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 7A is an exploded perspective view of yet another exemplary femoral cut guide of the present invention;

FIG. 7B is an assembled perspective view of the femoral cut guide of FIG. 7A;

FIG. 8A is an exploded perspective view of still yet another exemplary femoral cut guide of the present invention;

FIG. 8B is an assembled perspective view of the femoral cut guide of FIG. 8A;

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
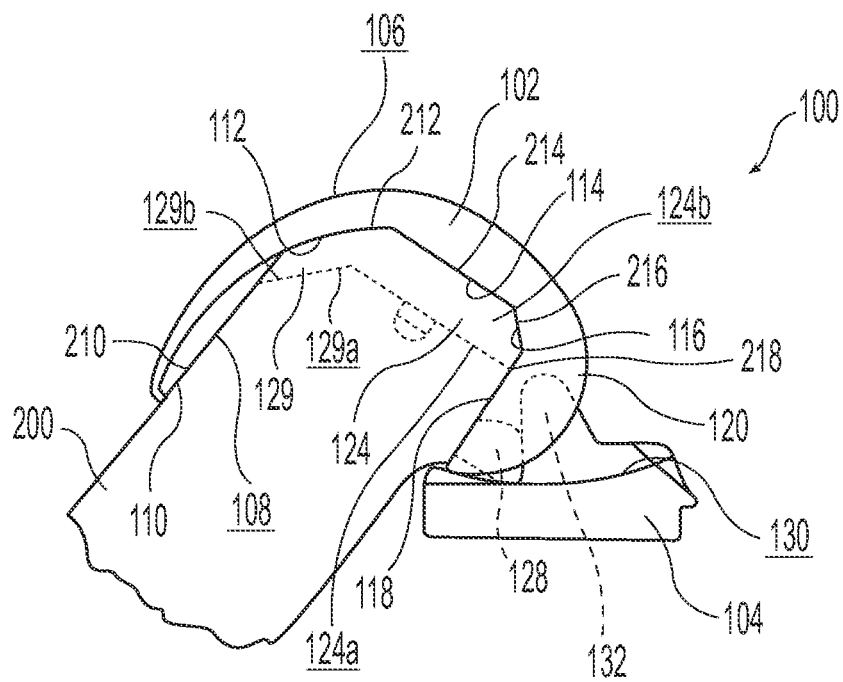
FIG. 1 is a medial elevational view of a posterior-stabilized knee implant in a flexed position, the knee implant including a prosthetic femoral component secured to a distal femur and a prosthetic tibial component.
Figure 2:
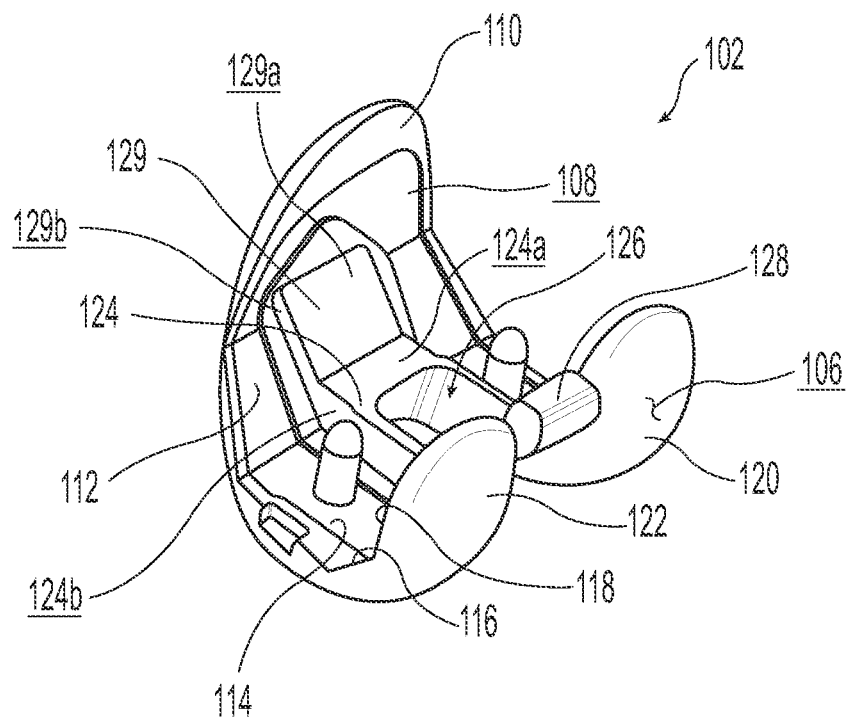
FIG. 2 is a posterior perspective view of the prosthetic femoral component of FIG. 1.

FIGS. 1 and 2 illustrate a posterior-stabilized knee implant 100. Knee implant 100 includes prosthetic femoral component 102 configured to attach to a patient's distal femur 200 and prosthetic tibial component 104 configured to attach to a patient's proximal tibia (not shown).

Prosthetic femoral component 102 of knee implant 100 includes articulating surface 106 that articulates against prosthetic tibial component 104, as shown in FIG. 1, and an opposing bone-contacting surface 108 that rests against the patient's resected distal femur 200. Bone-contacting surface 108 of prosthetic femoral component 102 includes anterior portion 110, anterior chamfer portion 112, distal portion 114, posterior chamfer portion 116, and posterior portion 118.

Distal femur 200 includes corresponding resected surfaces that are shaped to receive bone-contacting surface 108 of prosthetic femoral component 102. Specifically, distal femur 200 includes anterior resected surface 210 that is shaped to receive anterior portion 110 of bone-contacting surface 108, anterior chamfer resected surface 212 that is shaped to receive anterior chamfer portion 112 of bone-contacting surface 108, distal resected surface 214 that is shaped to receive distal portion 114 of bone-contacting surface 108, posterior chamfer resected surface 216 that is shaped to receive posterior chamfer portion 116 of bone-contacting surface 108, and posterior resected surface 218 that is shaped to receive posterior portion 118 of bone-contacting surface 108.

Also, prosthetic femoral component 102 of knee implant 100 includes medial and lateral condyles 120, 122. Between medial and lateral condyles 120, 122, prosthetic femoral component 102 includes box 124 that defines a central opening 126. As shown in FIGS. 1 and 2, side surfaces 124b of box 124 project proximally from distal portion 114 of bone-contacting surface 108, with top surface 124a of box 124 extending posteriorly from anterior chamfer portion 112 toward posterior portion 118 of bone-contacting surface 108. Box 124 may include anterior projection 129 having top surface 129a and side surfaces 129b, as shown in FIGS. 1 and 2. Also, between medial and lateral condyles 120, 122, prosthetic femoral component 102 includes cam 128.

Prosthetic tibial component 104 of knee implant 100 includes articulating surface 130 that articulates against prosthetic femoral component 102, as shown in FIG. 1. Prosthetic tibial component 104 also includes spine 132 that extends proximally from articulating surface 130. When the patient's knee joint is extended, spine 132 is received freely within opening 126 of box 124 of prosthetic femoral component 102. When the patient's knee joint is flexed, as shown in FIG. 1, spine 132 abuts cam 128 of prosthetic femoral component 102 to resist posterior translation of prosthetic tibial component 104 relative to prosthetic femoral component 102.

Figure 3:
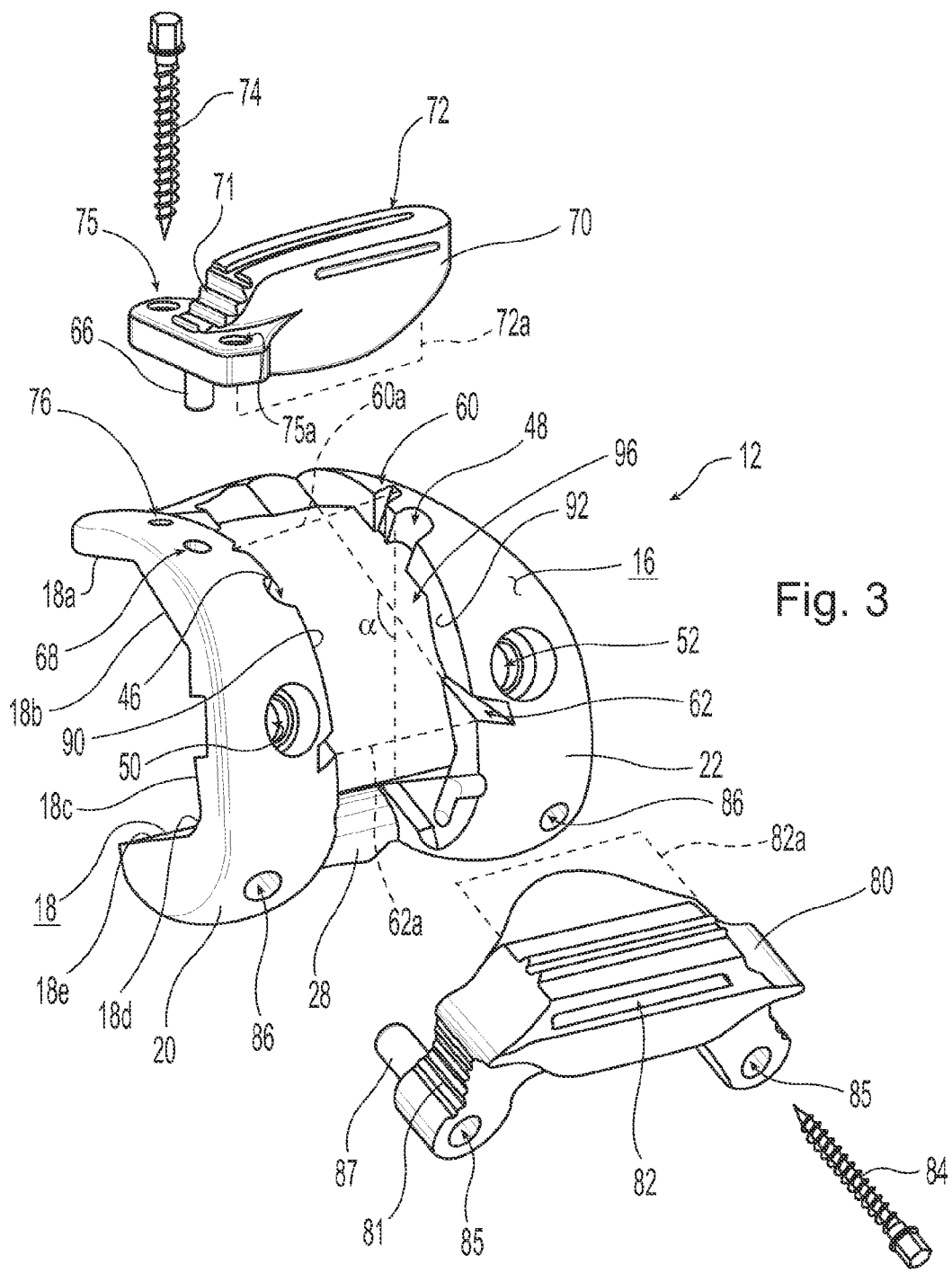
FIG. 3 is an exploded perspective view of an exemplary femoral cut guide of the present invention, the femoral cut guide including a removable box cut guide and a removable posterior cut guide.

Referring to FIG. 3, femoral cut guide 12 is provided to prepare the patient's distal femur to receive a prosthetic femoral component, such as the posteriorly-stabilized prosthetic femoral component 102 of FIGS. 1 and 2. More particularly, femoral cut guide 12 is provided to remove bone from distal femur 200 to accommodate box 124 and anterior projection 129 of prosthetic femoral component 102 of FIGS. 1 and 2.

As shown by comparing FIGS. 2 and 3, femoral cut guide 12 of the present invention is substantially identical in size and shape to prosthetic femoral component 102 of knee implant 100. For example, femoral cut guide 12 may include articulating surface 16 that is substantially identical in size and shape to articulating surface 106 of prosthetic femoral component 102, medial and lateral condyles 20, 22, that are substantially identical in size and shape to medial and lateral condyles 120, 122, of prosthetic femoral component 102, and cam 28 that is substantially identical in size and shape to cam 128 of prosthetic femoral component 102. Also, femoral cut guide 12 may include bone-contacting surface 18 that is substantially identical in size and shape to bone-contacting surface 108 of prosthetic femoral component 102, such that bone-contacting surface 18 includes anterior portion 18a, anterior chamfer portion 18b, distal portion 18c, posterior chamfer portion 18d, and posterior portion 18e. Therefore, in addition to guiding cutting of the patient's distal femur 200, femoral cut guide 12 may serve as a trial or provisional component used to reduce and test the prepared knee joint before implanting the final prosthetic femoral component 102.

Before mounting femoral cut guide 12 onto the patient's distal femur 200 (FIG. 1), a surgeon may first ream the patient's intramedullary canal (not shown). The prepared intramedullary canal may be used as a guide to reference various tools and cut guides throughout the knee arthroplasty procedure.

Next, the surgeon may attach one or more preliminary cut guides to the patient's distal femur 200 to make any preliminary resections. For example, one or more preliminary cut guides may be attached to the patient's distal femur 200 to prepare anterior resected surface 210 that will later receive anterior portion 110 of prosthetic femoral component 102, anterior chamfer resected surface 212 that will later receive anterior chamfer portion 112 of prosthetic femoral component 102, distal resected surface 214 that will later receive distal portion 114 of prosthetic femoral component 102, posterior chamfer resected surface 216 that will later receive posterior chamfer portion 116 of prosthetic femoral component 102, and posterior resected surface 218 that will later receive posterior portion 118 of prosthetic femoral component 102. Suitable preliminary cut guides include the "5-in-1 Femoral Saw Guide" and the "4-in-1 Femoral Cutting Guide," both of which are available from Zimmer, Inc. of Warsaw, Ind.

The surgeon may make any necessary adjustments to the size and/or location of femoral cut guide 12 before anchoring femoral cut guide 12 in place. For example, the surgeon may ensure that anterior portion 18a, anterior chamfer portion 18b, distal portion 18c, posterior chamfer portion 18d, and posterior portion 18e of bone-contacting surface 18 of femoral cut guide 12 rest properly against anterior resected surface 210, anterior chamfer resected surface 212, distal resected surface 214, posterior chamfer resected surface 216, and posterior resected surface 218 of distal femur 200, respectively. Also, the surgeon may ensure that femoral cut guide 12 is centered medially/laterally on the patient's distal femur 200 and that femoral cut guide 12 properly spans the patient's distal femur 200. The surgeon may also guide femoral cut guide 12 into place on the patient's distal femur 200 by referencing the patient's intramedullary canal (not shown). Because femoral cut guide 12 is substantially identical in size and shape to prosthetic femoral component 102, the location of femoral cut guide 12 on the patient's distal femur 200 will correspond to the location of prosthetic femoral component 102 on the patient's distal femur 200 (FIGS. 1 and 2). If femoral cut guide 12 does not properly fit the patient's bone, the surgeon may select a different size of femoral cut guide 12, which will correspond to a different size of prosthetic femoral component 102. If necessary, the surgeon may also re-cut the patient's distal femur 200.

Then, the surgeon may anchor femoral cut guide 12 to the patient's distal femur 200. As shown in FIG. 3, femoral cut guide 12 includes apertures 50, 52, that are sized to receive bone screws and/or pins for anchoring femoral cut guide 12 to the patient's distal femur 200. Before making any cuts using femoral cut guide 12, the surgeon may use femoral cut guide 12 as a trial or provisional component to reduce and test the partially-prepared knee joint before implanting the final prosthetic femoral component 102 (FIGS. 1 and 2).

With femoral cut guide 12 secured in place, the surgeon may prepare the patient's distal femur 200 to receive box 124 and anterior projection 129 of prosthetic femoral component (FIGS. 1 and 2). The order of the following resection steps using femoral cut guide 12 may be varied.

Figure 4:
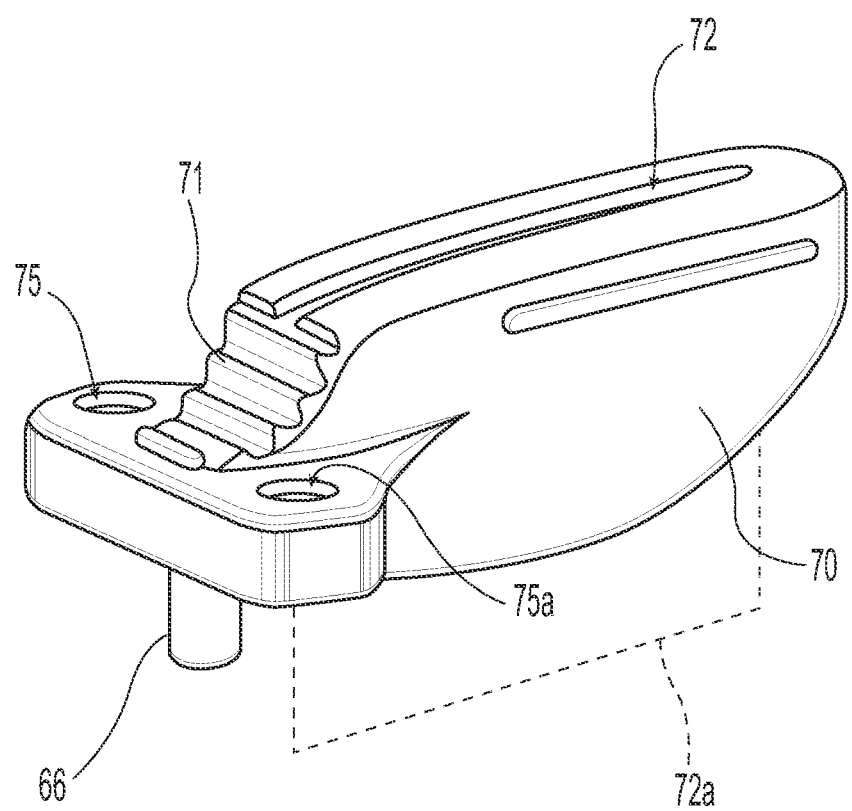
FIG. 4 is a perspective view of the box cut guide of FIG. 3.

Femoral cut guide 12 includes a detachable box cut guide 70, as shown in FIGS. 3 and 4. Box cut guide 70 defines box guide slot 72. Although the illustrated box cut guide 70 includes a reference surface that defines a captured guide slot 72, it is also within the scope of the present invention that a single reference surface of box cut guide 70 may define an exposed or non-captured guide slot 72. When box cut guide 70 is attached to femoral cut guide 12, box guide slot 72 in box cut guide 70 corresponds to and partially overlaps box guide slot 60 in femoral cut guide 12. Box cut guide 70 may include a textured surface 71 or handles (not shown) to improve the surgeon's ability to grip and manipulate box cut guide 70.

In operation, the surgeon may insert a reciprocating or oscillating saw blade (not shown) into box guide slot 72 and drag the blade along plane 72a of box cut guide 70 (which corresponds to plane 60a of femoral cut guide 12) to prepare the surface of the patient's distal femur 200 that will later receive box 124 of prosthetic femoral component 102 (FIGS. 1 and 2). Like box 124 of prosthetic femoral component 102 (FIGS. 1 and 2), planes 60a, 72a (FIG. 3) extend in an anterior/posterior direction. More particularly, planes 60a, 72a, extend in an anterior/posterior direction from anterior chamfer portion 18b to posterior portion 18e of bone-contacting surface 18 of femoral cut guide 12.

Box cut guide 70 may be removably attached to femoral cut guide 12 and, optionally, to the patient's bone using one or more suitable fasteners. In the illustrated embodiment of FIG. 3, box cut guide 70 includes at least one screw 74 that extends through aperture 75 in box cut guide 70, through aperture 76 in femoral cut guide 12, and into the patient's bone. Box cut guide 70 also includes one leg 66 that extends into bore 68 of femoral cut guide 12 to prevent box cut guide 70 from rotating freely relative to femoral cut guide 12.

Figure 6:
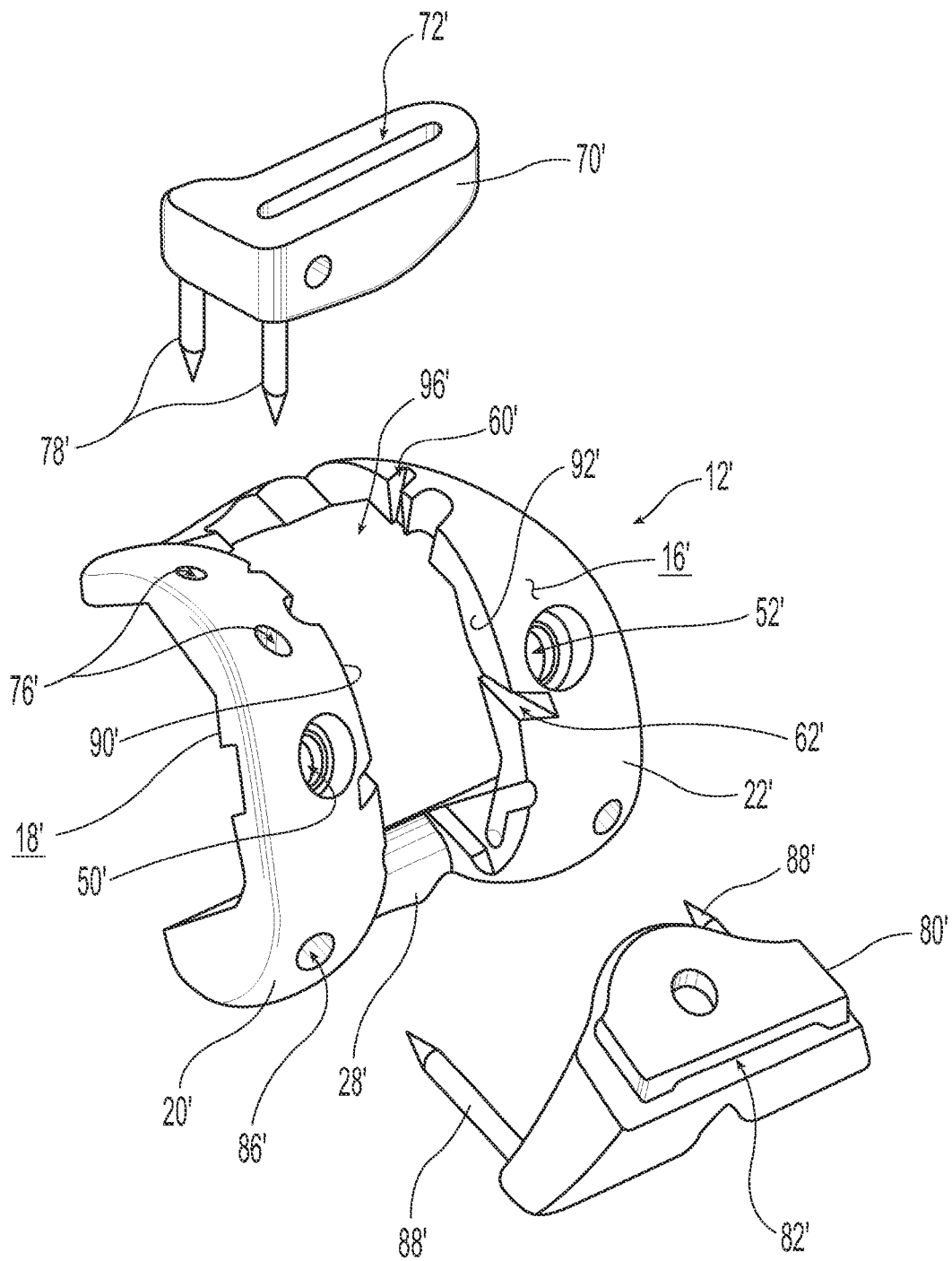
FIG. 6 is an exploded perspective view of another exemplary femoral cut guide of the present invention.

In the illustrated embodiment of FIG. 6, box cut guide 70' includes pins 78' that extend through apertures 76' in femoral cut guide 12' and into the patient's bone. The two pins 78' cooperate to prevent box cut guide 70' from rotating freely relative to femoral cut guide 12'.

In the illustrated embodiment of FIGS. 7A and 7B, box cut guide 70" includes screw 74" that extends through aperture 75" in box cut guide 70", through aperture 76" in femoral cut guide 12", and into the patient's bone. Box cut guide 70" also includes two legs 66" that extend into bores 68" of femoral cut guide 12" to prevent box cut guide 70" from rotating freely relative to femoral cut guide 12". Unlike pins 78' of box cut guide 70' (FIG. 6), legs 66" of box cut guide 70" may be received within femoral cut guide 12" without extending into the patient's bone. As shown in FIG. 7A, legs 66" are located on either side of screw 74" in box cut guide 70", and bores 68" are located on either side of aperture 76" in femoral cut guide 12".

In the illustrated embodiment of FIGS. 8A and 8B, box cut guide 70'" includes screw 74'" that extends through aperture 75'" in box cut guide 70'", through a non-circular aperture 76'" in femoral cut guide 12'", and into the patient's bone. Box cut guide 70'" also includes a non-circular leg 66'" surrounding screw 74'" that extends into the non-circular aperture 76'" along with screw 74'" to prevent box cut guide 70'" from rotating freely relative to femoral cut guide 12'".

According to an exemplary embodiment of the present invention, box cut guide 70 is selectively rotatable relative to femoral cut guide 12, such that box cut guide 70 may be used with both right-leg and left-leg femoral cut guides 12. For example, in the illustrated embodiment of FIG. 3, box cut guide 70 may be rotated 180 degrees about leg 66 and coupled to a right-leg femoral cut guide that is the mirror image of the left-leg femoral cut guide 12 shown in FIG. 3. Box cut guide 70 includes an additional aperture 75a for screw 74 that may be used instead of aperture 75 when rotated to accommodate the other leg. In the illustrated embodiment of FIG. 6, box cut guide 70' may be rotated 180 degrees about an axis located between pins 78', and pins 78' may be inserted into the opposite apertures 76' of a right-leg femoral cut guide. For example, the proximal-most pin 78' that is shown being inserted into the proximal-most aperture 76' of the left-leg femoral cut guide 12' may be inserted into the other, distalmost aperture of a right-leg femoral cut guide. In the illustrated embodiment of FIG. 7A, box cut guide 70'' may be rotated 180 degrees about screw 74'' and legs 66'' may be inserted into the opposite apertures 68'' of a right-leg femoral cut guide. In the illustrated embodiment of FIG. 8A, box cut guide 70''' may be rotated 180 degrees about leg 66'''.

Figure 5:
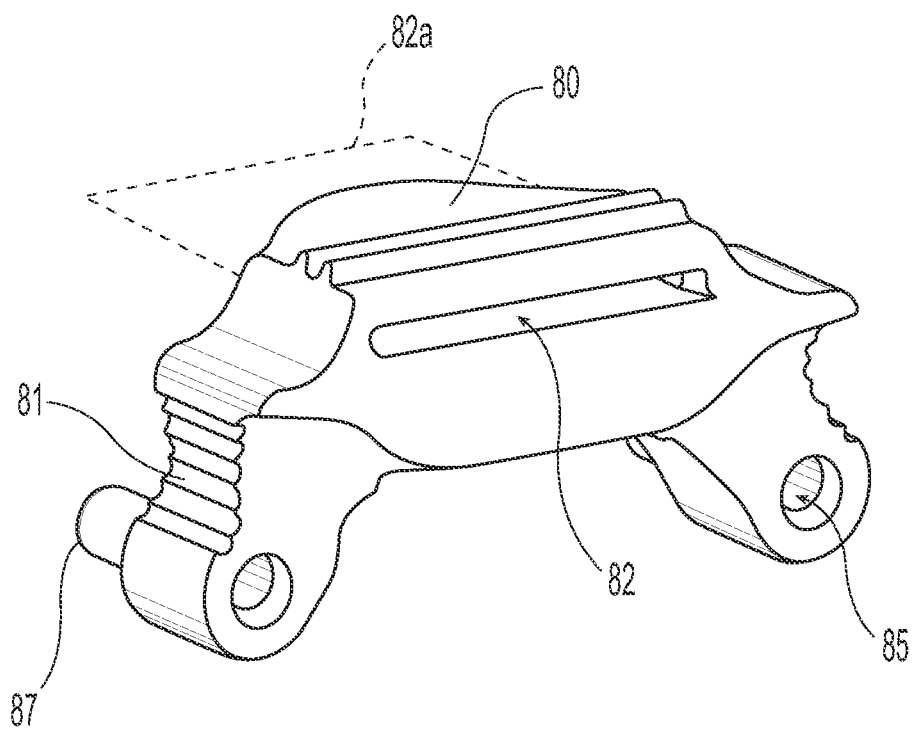
FIG. 5 is an anterior perspective view of the posterior cut guide of FIG. 3.

Femoral cut guide 12 further includes a detachable projection cut guide 80, as shown in FIGS. 3 and 5. Projection cut guide 80 defines projection guide slot 82. Although the illustrated projection cut guide 80 includes a reference surface that defines a captured guide slot 82, it is also within the scope of the present invention that a single reference surface of projection cut guide 80 may define an exposed or non-captured guide slot 82. When projection cut guide 80 is attached to femoral cut guide 12, projection guide slot 82 in projection cut guide 80 corresponds to and partially overlaps projection guide slot 62 in femoral cut guide 12. Projection cut guide 80 may include a textured surface 81 or handles (not shown) to improve the surgeon's ability to grip and manipulate projection cut guide 80.

In operation, the surgeon may insert a reciprocating or oscillating saw blade (not shown) into projection guide slot 82 and drag the blade along plane 82a of projection cut guide 80 (which corresponds to plane 62a of femoral cut guide 12) to prepare the surface of the patient's femur that will later receive anterior projection 129 of prosthetic femoral component 102 (FIGS. 1 and 2). Like anterior projection 129 of prosthetic femoral component 102 (FIGS. 1 and 2), planes 62a, 82a (FIG. 3) extend in a proximal, slightly anterior direction. More particularly, planes 62a, 82a, extend in a proximal, slightly anterior direction from distal portion 18c to anterior portion 18a of bone-contacting surface 18 of femoral cut guide 12.

Projection cut guide 80 may be removably attached to femoral cut guide 12 and, optionally, to the patient's bone using one or more suitable fasteners. In the illustrated embodiment of FIGS. 3 and 5, projection cut guide 80 includes at least one screw 84 that extends through aperture 85 in projection cut guide 80, through apertures 86 in femoral cut guide 12, and into the patient's bone. Projection cut guide 80 also includes legs 87 that extend into apertures 86 of femoral cut guide 12 to prevent projection cut guide 80 from rotating freely relative to femoral cut guide 12.

In the illustrated embodiment of FIG. 6, projection cut guide 80' includes one or more pins 88' instead of screws 84 (FIG. 3). Pins 88' extend through apertures 86' in femoral cut guide 12' and into the patient's bone. The two pins 88' cooperate to prevent projection cut guide 80' from rotating freely relative to femoral cut guide 12'.

To complete the resections of distal femur 200 (FIG. 1), the surgeon may detach box cut guide 70 and projection cut guide 80 from femoral cut guide 12. Then, the surgeon may drag a reciprocating or oscillating saw blade (not shown) along side walls 90, 92, of femoral cut guide 12. The surgeon may attempt to insert the blade only to the depth of planes 60a, 62a. As shown in FIG. 3, planes 60a, 62a, define an obtuse angle α therebetween.

The bone removed from distal femur 200 using femoral cut guide 12 will accommodate box 124 and projection 129 of prosthetic femoral component 102 (FIGS. 1 and 2). More particularly, the bone removed from distal femur 200 along plane 60a will accommodate top surface 124a of box 124, the bone removed from distal femur 200 along plane 62a will accommodate top surface 129a of projection 129, and the bone removed from distal femur 200 along side walls 90, 92, will accommodate side surfaces 124b of box 124 and side surfaces 129b of projection 129.

Figure 9A:
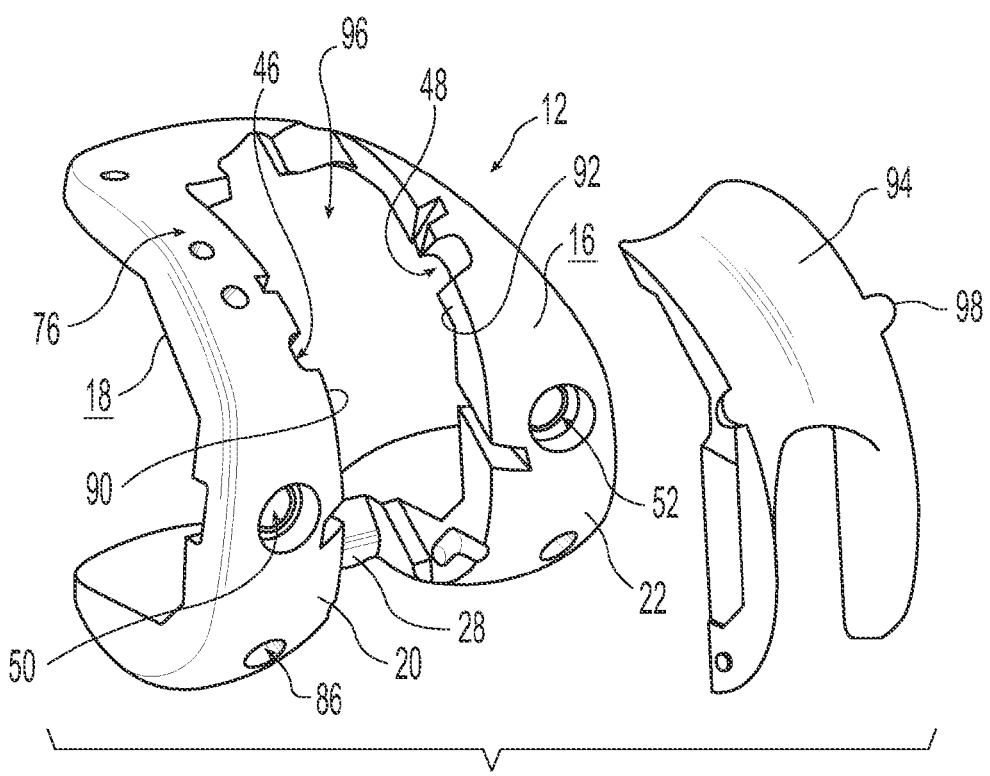
FIG. 9A is an exploded perspective view a trial trochlear component for use in conjunction with the femoral cut guides of the present invention.
Figure 9B:
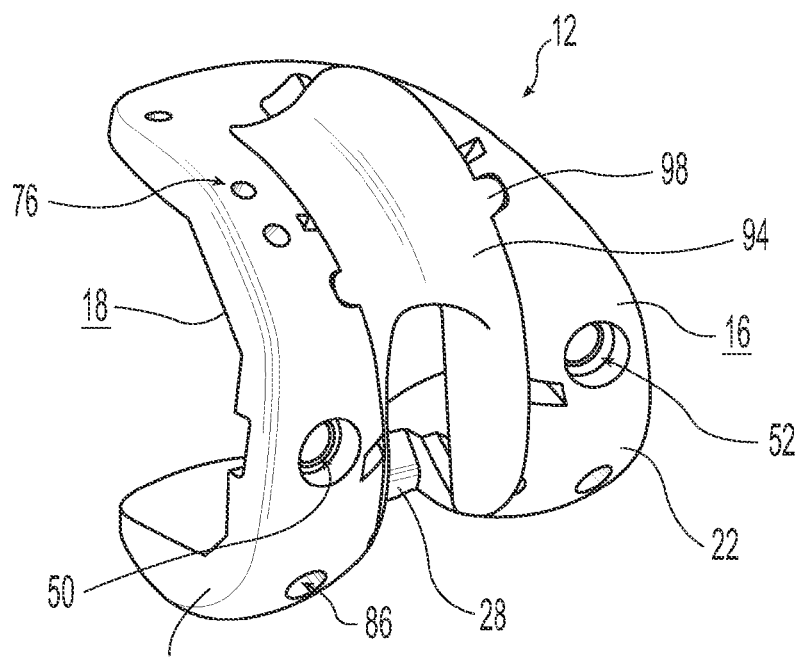
FIG. 9B is an assembled perspective view of the trial trochlear component and the femoral cut guide of FIG. 9A.

With box cut guide 70 and projection cut guide 80 removed, the surgeon may use femoral cut guide 12 as a trial or provisional component to reduce and test the prepared knee joint before implanting the final prosthetic femoral component 102 (FIGS. 1 and 2). In certain embodiments, the surgeon may couple a trial trochlear component 94, as shown in FIGS. 9A and 9B, to femoral cut guide 12 in opening 96 between side walls 90, 92. Trial trochlear component 94 may include protrusions 98 that are sized for receipt into corresponding recesses 46, 48, of femoral cut guide 12 (FIG. 3) to couple the components together. When assembled, the surgeon may verify proper articulation of femoral cut guide 12 against the patient's adjacent patella and tibia (not shown).

Advantageously, the ability to test the prepared knee joint using femoral cut guide 12 allows the surgeon to visualize the location of the final prosthetic femoral component 102 (FIGS. 1 and 2) before cutting the patient's bone to receive box 124 and projection 129 of prosthetic femoral component 102. Also, the ability to test the prepared knee joint using femoral cut guide 12 eliminates the additional steps of removing femoral cut guide 12 and replacing it with a separate trial component. Moreover, the removable box cut guide 70 and projection cut guide 80 allow a single femoral cut guide 12 to be used for multiple cuts.

According to an exemplary embodiment of the present invention, femoral cut guide 12 may be able to receive box cut guides 70 and/or projection cut guides 80 of various shapes and sizes. In this embodiment, a single femoral cut guide 12 may be used to prepare distal femur 200 (FIG. 1) to receive various prosthetic femoral components, such as the NexGen® LPS Femoral Component and the NexGen® Legacy® LCCK Femoral Component, both of which are available from Zimmer, Inc. of Warsaw, Ind. To prepare distal femur 200 to receive the LPS Femoral Component (which may be substantially similar to prosthetic femoral component 102 of FIG. 2), the illustrated box cut guide 70 may be used with femoral cut guide 12. The LCCK Femoral Component may have a taller, more proximally oriented box than the LPS Femoral Component. To prepare distal femur 200 to receive the taller, more proximally oriented box of the LCCK Femoral Component, a second box cut guide (not shown) may be provided with a more proximally oriented guide slot than the first box cut guide 70 and may be used with the same femoral cut guide 12 as the first box cut guide 70. Advantageously, the surgeon may make intraoperative changes without having to remove and replace femoral cut guide 12.

According to another exemplary embodiment of the present invention, box cut guides 70 and/or projection cut guides 80 may be adjustably coupled to femoral cut guide 12. For example, the depth and/or orientation of each box cut guide 70 and each projection cut guide 80 may be adjusted relative to femoral cut guide 12. Returning to the previous example, femoral cut guide 12 may have a first set of holes for receiving box cut guide 70 to accommodate the LPS Femoral Component and a second set of holes for receiving box cut guide 70 in a more proximal position to accommodate the taller, more proximally oriented box of the LCCK Femoral Component. Advantageously, the surgeon may make intraoperative changes without having to remove and replace femoral cut guide 12.

Figure 10:
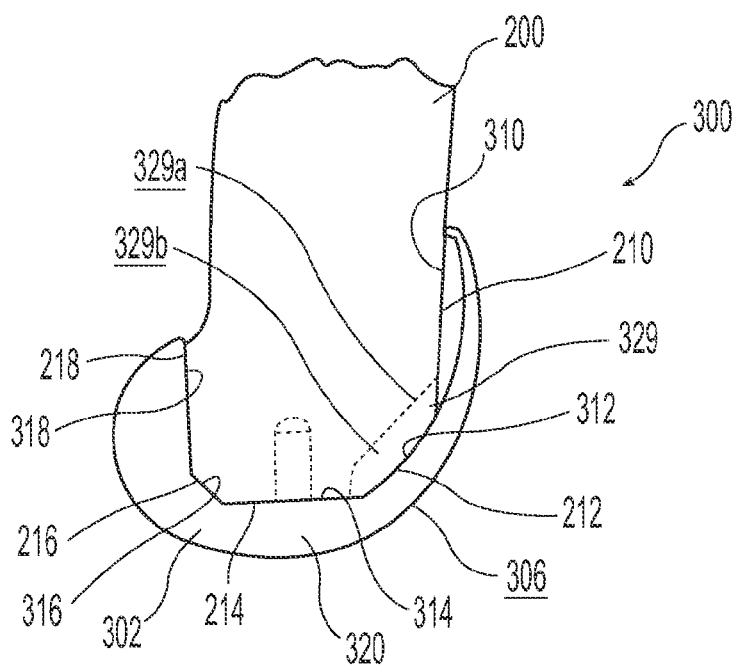
FIG. 10 is a medial elevational view of a cruciate-retaining knee implant in an extended position, the knee implant including a prosthetic femoral component secured to a distal femur.
Figure 11:
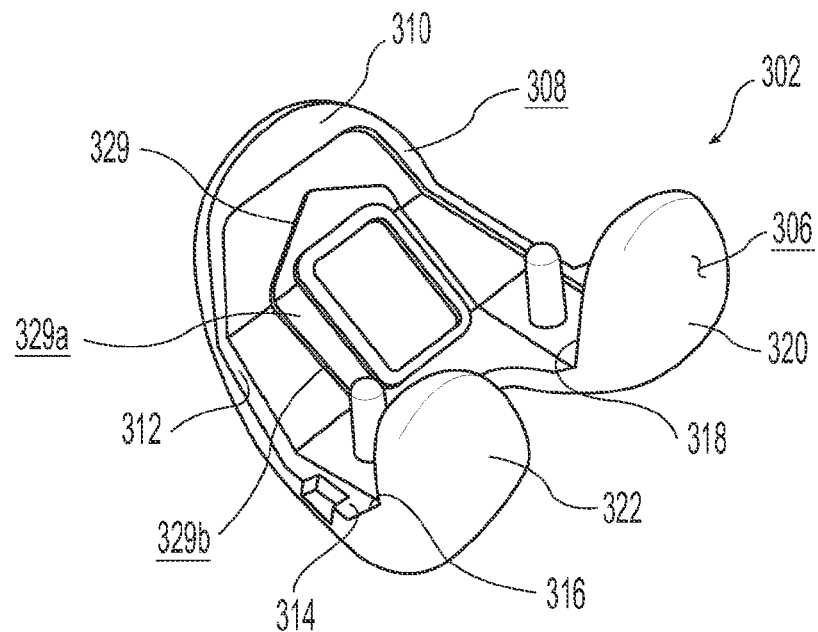
FIG. 11 is a posterior perspective view of the prosthetic femoral component of FIG. 10.

Referring next to FIGS. 10 and 11, a cruciate-retaining knee implant 300 is provided including prosthetic femoral component 302 configured to attach to a patient's distal femur 200. Prosthetic femoral component 302 may be similar to the NexGen® Complete Knee Solution Cruciate-Retaining (CR) Femoral Component, which is available from Zimmer, Inc. of Warsaw, Ind.

Prosthetic femoral component 302 of FIGS. 10 and 11 may include certain features that are similar to prosthetic femoral component 102 of FIGS. 1 and 2, except as described below. Prosthetic femoral component 302 of knee implant 300 includes articulating surface 306 and an opposing bone-contacting surface 308 that rests against the patient's resected distal femur 200. Bone-contacting surface 308 of prosthetic femoral component 302 includes anterior portion 310, anterior chamfer portion 312, distal portion 314, posterior chamfer portion 316, and posterior portion 318.

Prosthetic femoral component 302 of knee implant 300 also includes medial and lateral condyles 320, 322. Between medial and lateral condyles 320, 322, prosthetic femoral component 302 includes anterior box 329. As shown in FIGS. 10 and 11, side surfaces 329b of anterior box 329 project proximally from anterior chamfer portion 312 and distal portion 314 of bone-contacting surface 308, with top surface 329a of anterior box 329 extending posteriorly and distally from anterior portion 310 toward distal portion 314 of bone-contacting surface 308. When implanted on distal femur 200, anterior box 329 may extend proximally into the patient's bone to support and stabilize prosthetic femoral component 302.

Figure 12:
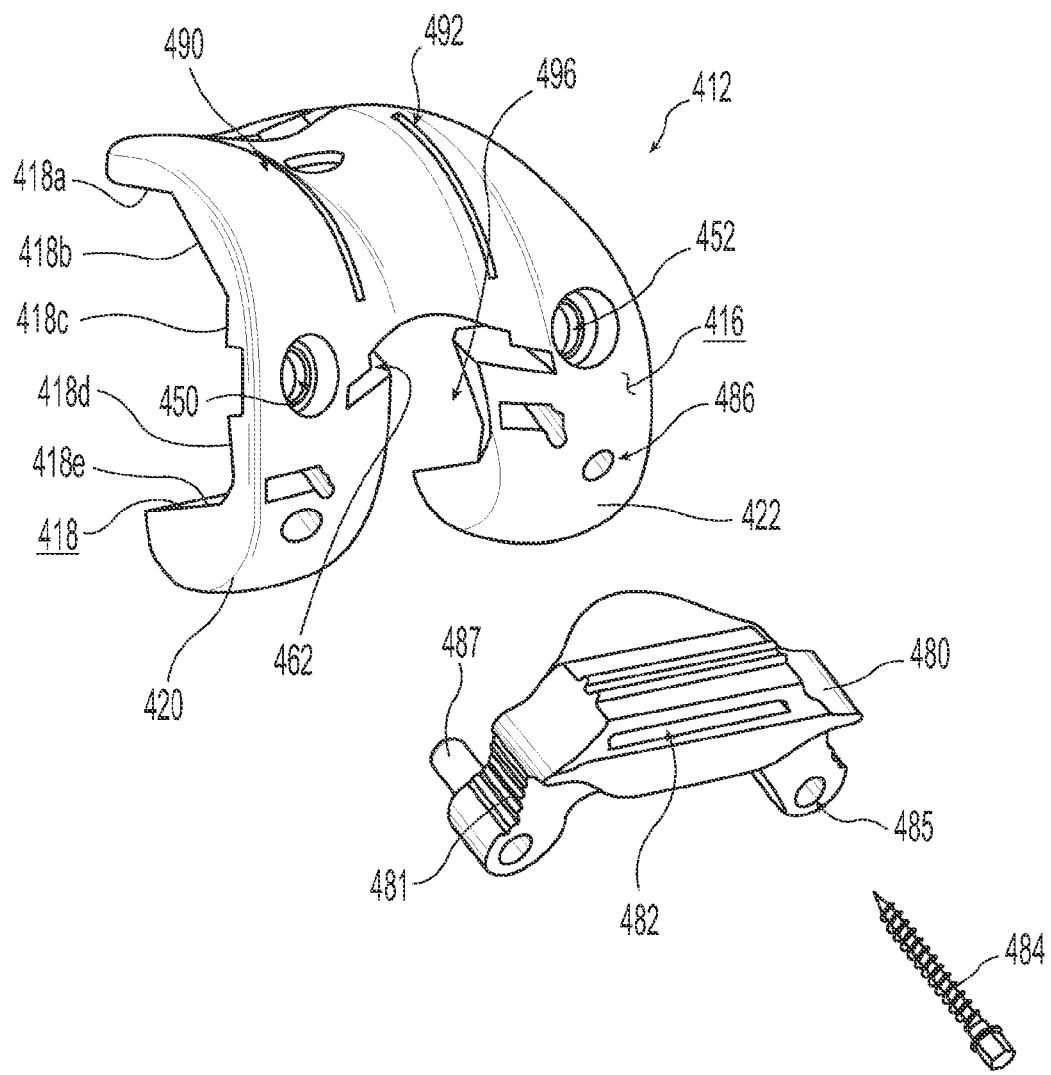
FIG. 12 is an exploded perspective view of still yet another exemplary femoral cut guide of the present invention, the femoral cut guide including a box cut guide.

Referring to FIG. 12, femoral cut guide 412 is provided to prepare the patient's distal femur to receive the cruciate-retaining prosthetic femoral component 302 of FIGS. 10 and 11. More particularly, femoral cut guide 412 is provided to remove bone from distal femur 200 to accommodate anterior box 329 of prosthetic femoral component 302. Femoral cut guide 412 of FIG. 12 may include certain features that are similar to femoral cut guide 12 of FIG. 3, femoral cut guide 12' of FIG. 6, femoral cut guide 12" of FIG. 7A, and/or femoral cut guide 12''' of FIG. 8A, with like reference numerals indicating like elements, except as described below.

As shown by comparing FIGS. 11 and 12, femoral cut guide 412 of the present invention is substantially identical in size and shape to prosthetic femoral component 302 of knee implant 300. For example, femoral cut guide 412 may include articulating surface 416 that is substantially identical in size and shape to articulating surface 306 of prosthetic femoral component 302, medial and lateral condyles 420, 422, that are substantially identical in size and shape to medial and lateral condyles 320, 322, of prosthetic femoral component 302, and bone-contacting surface 418 that is substantially identical in size and shape to bone-contacting surface 308 of prosthetic femoral component 302.

Femoral cut guide 412 also includes a detachable box cut guide 480, as shown in FIG. 12, which may be substantially similar or identical to projection cut guide 80 of FIG. 3. Box cut guide 480 defines box guide slot 482. Although the illustrated box cut guide 480 includes a reference surface that defines a captured guide slot 482, it is also within the scope of the present invention that a single reference surface of box cut guide 480 may define an exposed or non-captured guide slot 482. When box cut guide 480 is attached to femoral cut guide 412, box guide slot 482 in box cut guide 480 corresponds to and partially overlaps box guide slot 462 in femoral cut guide 412. Box cut guide 480 may include a textured surface 481 or handles (not shown) to improve the surgeon's ability to grip and manipulate box cut guide 480. In operation, the surgeon may insert a reciprocating or oscillating saw blade (not shown) into box guide slot 482 to prepare the surface of the patient's femur that will later receive anterior box 329 of prosthetic femoral component 302 (FIGS. 10 and 11).

Box cut guide 480 may be removably attached to femoral cut guide 412 and, optionally, to the patient's bone using one or more suitable fasteners. In the illustrated embodiment of FIG. 12, box cut guide 480 includes at least one screw 484 that extends through aperture 485 in box cut guide 480, through apertures 486 in femoral cut guide 412, and into the patient's bone. Box cut guide 480 also includes legs 487 that extend into apertures 486 of femoral cut guide 412 to prevent box cut guide 480 from rotating freely relative to femoral cut guide 412.

Femoral cut guide 412 further includes laterally spaced slots 490, 492. To complete the resections of distal femur 200 (FIG. 10), the surgeon may drag a reciprocating or oscillating saw blade (not shown) through slots 490, 492, of femoral cut guide 412 (which are similar in location and orientation to side walls 90, 92, of femoral cut guide 12).

The bone removed from distal femur 200 using femoral cut guide 412 will accommodate anterior box 329 of prosthetic femoral component 302 (FIG. 10). More particularly, the bone removed from distal femur 200 using box cut guide 480 will accommodate top surface 329a of anterior box 329 and the bone removed from distal femur 200 along slots 490, 492, will accommodate side surfaces 329b of anterior box 329.

With box cut guide 480 removed, the surgeon may use femoral cut guide 412 as a trial or provisional component to reduce and test the prepared knee joint before implanting prosthetic femoral component 302 (FIGS. 10 and 11). Advantageously, the ability to test the prepared knee joint using femoral cut guide 412 allows the surgeon to visualize the location of the final prosthetic femoral component 302 (FIGS. 10 and 11) before cutting the patient's bone to receive anterior box 329 of prosthetic femoral component 302. Also, the ability to test the prepared knee joint using femoral cut guide 412 eliminates the additional steps of removing femoral cut guide 412 and replacing it with a separate trial component. Moreover, the removable box cut guide 480 allows a single femoral cut guide 412 to be used for multiple cuts.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A femoral cut guide for preparing a distal femur to receive a prosthetic femoral component, the prosthetic femoral component including a first articulating surface and an opposing first bone-contacting surface that rests against the distal femur, the prosthetic femoral component further including a box that projects proximally from the first bone-contacting surface, the femoral cut guide comprising:

a body having a second articulating surface that is shaped to replicate the first articulating surface and a second bone-contacting surface that is shaped to replicate the first bone-contacting surface, the body including a medial side and a lateral side that define an opening therebetween;

a box cut guide removably coupled to the body such that the box cut guide spans the medial and lateral sides of the body across the opening, the box cut guide including a first reference surface located in a first cut plane; and a second cut guide removably coupled to the body at a different location than the box cut guide such that the second cut guide spans the medial and lateral sides of the body across the opening, the second cut guide including a second reference surface that is located in a second cut plane, the second cut plane intersecting the first cut plane at an obtuse angle.

2. The femoral cut guide of claim 1, wherein the box cut guide comprises a guide slot that includes the first reference surface and that is sized to receive a cutting tool therein.

3. The femoral cut guide of claim 1, wherein the first reference surface of the box cut guide comprises an unenclosed surface against which a cutting tool can be arranged.

4. The femoral cut guide of claim 1, wherein the second cut guide comprises a guide slot that includes the second reference surface and that is sized to receive a cutting tool therein.

5. The femoral cut guide of claim 1, wherein the second reference surface of the second cut guide comprises an unenclosed surface against which a cutting tool can be arranged.

6. The femoral cut guide of claim 1, wherein the box cut guide is rotatable 180 degrees about an axis between a first orientation and a second orientation, the box cut guide including at least one protrusion that engages the body to retain the box cut guide in one of the first and second orientations, and wherein one of the first and second orientations arranges the box cut guide to span the medial and lateral sides of the body across the opening.

7. The femoral cut guide of claim 1, wherein the opening comprises a medial side and a lateral side planar reference surface, each of the medial side and lateral side planar reference surfaces configured to guide a cutting tool through the opening in a direction substantially perpendicular to the first and second cut planes.

8. The femoral cut guide of claim 1, wherein the box cut guide comprises a textured surface configured to aid manipulation of the box cut guide.

9. The femoral cut guide of claim 1, wherein the box cut guide comprises one or more handles configured to aid manipulation of the box cut guide.

10. The femoral cut guide of claim 1, wherein the box cut guide comprises a protrusion configured to extend into an aperture of the femoral cut guide to prevent rotation of the box cut guide relative to the femoral cut guide.

11. The femoral cut guide of claim 1, wherein each of the first and second bone-contacting surfaces includes an anterior portion, a distal portion, an anterior chamfer portion that extends obtusely from the anterior and distal portions, a posterior portion, and a posterior chamfer portion that extends obtusely from the distal and posterior portions.

12. The femoral cut guide of claim 1, further comprising a trial trochlear component received in the opening.

13. A femoral cut guide for preparing a distal femur to receive a prosthetic femoral component, the prosthetic femoral component including a first articulating surface and an opposing first bone-contacting surface that rests against the distal femur, the prosthetic femoral component further including a box that projects proximally from the first bone-contacting surface, the femoral cut guide comprising:
    a body having a second articulating surface that is shaped to replicate the first articulating surface and a second bone-contacting surface that is shaped to replicate the first bone-contacting surface, the body including a medial side and a lateral side;
    a box cut guide arranged to span the medial and lateral sides of the body, the box cut guide including a first reference surface located in a first cut plane; and
    a second cut guide arranged to span the medial and lateral sides of the body at a different location than the box cut guide, the second cut guide including a second reference surface that is located in a second cut plane, the second cut plane intersecting the first cut plane at an obtuse angle.

14. The femoral cut guide of claim 13, wherein the box cut guide comprises a guide slot that includes the first reference surface and that is sized to receive a cutting tool therein.

15. The femoral cut guide of claim 13, wherein the first reference surface of the box cut guide comprises an unenclosed surface against which a cutting tool can be arranged.

16. The femoral cut guide of claim 13, wherein the second cut guide comprises a guide slot that includes the second reference surface and that is sized to receive a cutting tool therein.

17. The femoral cut guide of claim 13, wherein the second reference surface of the second cut guide comprises an unenclosed surface against which a cutting tool can be arranged.

18. The femoral cut guide of claim 13, wherein the box cut guide is rotatable 180 degrees about an axis between a first orientation and a second orientation, and wherein one of the first and second orientations arranges the box cut guide to span the medial and lateral sides of the body.

19. The femoral cut guide of claim 13, wherein the body comprises a medial side guide slot and a lateral side guide slot, each of the medial side and lateral side slots configured to guide a cutting tool in a direction substantially perpendicular to the first and second cut planes.

20. The femoral cut guide of claim 13, wherein the box cut guide comprises a protrusion configured to extend into an aperture of the femoral cut guide to prevent rotation of the box cut guide relative to the femoral cut guide.

* * * * *